United States Patent
Van Kasteren-Westerneng et al.

(10) Patent No.: US 12,023,374 B2
(45) Date of Patent: Jul. 2, 2024

(54) **VACCINE FOR PROTECTION AGAINST *STREPTOCOCCUS suis***

(71) Applicant: Intervet Inc., Madison, NJ (US)

(72) Inventors: Theodora Johanna Van Kasteren-Westerneng, Arnhem (NL); Antonius Arnoldus Christiaan Jacobs, Kessel (NL)

(73) Assignee: Intervet Inc., Rahway, NJ (US)

( * ) Notice: Subject to any disclaimer, the term of this patent is extended or adjusted under 35 U.S.C. 154(b) by 629 days.

(21) Appl. No.: 17/294,706

(22) PCT Filed: Nov. 22, 2019

(86) PCT No.: PCT/EP2019/082196
§ 371 (c)(1),
(2) Date: May 18, 2021

(87) PCT Pub. No.: WO2020/104640
PCT Pub. Date: May 28, 2020

(65) Prior Publication Data
US 2022/0001003 A1    Jan. 6, 2022

(30) Foreign Application Priority Data
Nov. 23, 2018    (EP) .................................... 18208081

(51) Int. Cl.
*A61K 39/12* (2006.01)
*A61K 39/00* (2006.01)

(52) U.S. Cl.
CPC ........ *A61K 39/12* (2013.01); *A61K 2039/545* (2013.01); *A61K 2039/55* (2013.01)

(58) Field of Classification Search
None
See application file for complete search history.

(56) References Cited

U.S. PATENT DOCUMENTS

2022/0001003 A1*  1/2022  Van Kasteren-Westerneng .......... A61K 39/092

FOREIGN PATENT DOCUMENTS

WO    2015181356 A1    12/2015
WO    2017005913 A1    1/2017

OTHER PUBLICATIONS

Alignment of SEQ 1 with Geneseq db access BJD29916 by Steele et al. in EP3795174 2015.*
European search report for application No. 18208081 dated Feb. 15, 2019.
Goyette-Desjardins, , G, et al, Protection against *Streptococcus suis* Sero type 2 Infection Using a Capsular Polysaccharide Glycoconjugate Vaccine, Infection and Immunity, 2016, pp. 2059-2075, vol. 84,No. 7.
Hu, et al, Complete Genome Sequence of Streptococcus suis Serotype 14 Strain JS14', Journal of Bacteriology, May 2011, pp. 2375-2376, vol. 193, No. 9.
Seele, J et al, The immunoglobulin M-degrading enzyme of *Streptococcus suis*, Idessuiss, is involved in complement evasion, Veterinary research, 2015, pp. 45, vol. 46.
Seele, J et al, The immunoglobulin M-degrading enzyme of *Streptococcus suis*, IdeSsuis, is a highly protective antigen against serotype 2, Vaccine, 2015, pp. 2207-2212, vol. 33 No. 19, Elsevier, EP.

* cited by examiner

*Primary Examiner* — Shanon A. Foley
(74) *Attorney, Agent, or Firm* — David J. Kerwick

(57) ABSTRACT

The present invention pertains to a vaccine comprising an IgM protease antigen of *Streptococcus suis*, for use in a method for protecting a pig against *Streptococcus suis*, characterised in that the IgM protease antigen is a protein according to SEQ ID NO:1.

15 Claims, No Drawings
Specification includes a Sequence Listing.

SEQUENCE LISTING

<160> NUMBER OF SEQ ID NOS: 1

<210> SEQ ID NO 1
<211> LENGTH: 1108
<212> TYPE: PRT
<213> ORGANISM: Streptococcus suis

<400> SEQUENCE: 1

Met Val Val Thr Gly Val Asn Glu Ile Ile Glu Glu Ser Gln Val Lys
1               5                   10                  15

Asp Glu Val Ser Ile Glu Ser Glu Lys Asn Glu Ser Leu Asp Gly Ser
                20                  25                  30

Asn Ile Glu Ile Val Glu Glu Ile Ala Asp Asn Ile Pro Ser Pro Val
            35                  40                  45

Ile Ala Glu Gly Glu Val Ala Val Glu Met Lys Val Asp Arg Gly Thr
        50                  55                  60

Glu Asn Val Val Ser Arg Asn Asp Thr Glu Val Thr Thr Ser Glu Gln
65                  70                  75                  80

Asn Gln Ile Glu Val Thr Glu Thr Lys Glu Ile Leu Asn Gln Thr Ser
                85                  90                  95

Tyr Gln Thr Glu Ser Gly Glu Gln Arg Gln Ile Ile Trp Ala His Gly

-continued

```
                100                 105                 110
Ile Thr Pro Pro Ala Met Glu Gln Ser Gly Gly Phe Val Lys Glu Lys
            115                 120                 125
Tyr Gly Asp Tyr Leu Asn Tyr Thr Ala Pro Phe Glu Ala Gly Lys Gly
        130                 135                 140
Tyr Tyr Asp Thr Asn Lys Ser Leu Asn Ala Ser Phe Ile Asp Leu Asn
145                 150                 155                 160
Leu Cys Phe Ala Ala Val Ser Ser Asn Met Val His Trp Trp Leu Glu
                165                 170                 175
Gln Asn Ser Ser Tyr Val Glu Arg Tyr Leu Lys Glu Lys Lys Gly Thr
            180                 185                 190
Val Asn Val Glu Glu Asn Tyr Ala Ile Thr Asp Leu Arg Arg Tyr Ile
        195                 200                 205
Asn Ser Phe Gln Asn Gln Gln Asn Ser Arg Val Phe Asp Met Phe Lys
    210                 215                 220
Thr Tyr Tyr Gly Tyr Arg Thr Asn Gly Phe Val Ser Asp Ala Leu Val
225                 230                 235                 240
Asp Leu Phe Ile Asn Gly Tyr Lys Pro Lys Ala Gln Gly Gly Val Asn
                245                 250                 255
Leu Glu Asp Ser Gln Leu Val Pro Asp Ser Arg Gly Gly Phe Phe Tyr
            260                 265                 270
Asp Val Phe Lys Glu Lys Lys Leu Thr Asn Arg Ile Phe Ser Gly Ser
        275                 280                 285
Tyr Glu Arg Phe Gly Glu Asp Val Arg Thr Val Leu Glu Ser Lys Gly
    290                 295                 300
Leu Leu Gly Leu Thr Tyr Arg Thr Leu Gly Tyr Ala Thr His Ile Val
305                 310                 315                 320
Thr Val Trp Gly Ala Glu Tyr Asp Asn Gln Gly Lys Ile Lys Ala Val
                325                 330                 335
Tyr Ile Thr Asp Ser Asp Asp Gln Gln Glu Gln Ile Gly Leu Lys Arg
            340                 345                 350
Met Gly Ile Thr Arg Asp Ala Ser Gly Asn Pro Arg Leu Asn Asn His
        355                 360                 365
Met Lys Asn Asn Ser Ala Gly Ala Leu Leu Asp Tyr Val His Thr Ile
    370                 375                 380
Arg Leu Gly Gln Asp Leu Trp Glu Glu Tyr Phe Asn Pro Leu Ala Lys
385                 390                 395                 400
Ala Lys Glu Thr Ala Ser Gln Thr Leu Ala Asp Thr Lys Lys Ala Leu
                405                 410                 415
Asp Leu Ser Ile Gln Gly Gln Ser Glu Leu Pro Glu Ser Met Arg Leu
            420                 425                 430
Ile Tyr Leu Glu Lys Leu Asn Asn Leu Tyr Asn Gln Gly Ile Leu Ser
        435                 440                 445
Ile Gln Lys Ala Glu Ser Ser Glu Met Leu Ser Gly Ala Leu Glu Asn
    450                 455                 460
Gly Leu Asn Ser Leu Lys Ser Leu Asp Phe Pro Ile Ser Glu Val Gly
465                 470                 475                 480
Asn Ala Leu Ala Pro Asp Leu Pro Val Gly Asp Arg Ser Thr Val Ser
                485                 490                 495
Asp Val Asp Ser Leu Ser Ser Gln Glu Thr Ser Ser Thr Asn Leu Glu
            500                 505                 510
Ala Asp Thr Glu Asn Ala Gly Ile Ile Ala Asp Gly Thr Asn Gln Leu
        515                 520                 525
```

-continued

His Phe Pro Val Glu Ala Gln Thr Thr Ser Ser Val Glu Ala Glu Gly
            530                 535                 540

Asp Asn Val Phe Glu Gln Glu Ala Asp Thr Leu Pro Ile Ile Ile Glu
545                 550                 555                 560

Asn Lys Asp Glu Phe Gly Ser Glu Leu Ser Arg Asn Met Gln Thr Ser
                565                 570                 575

Glu Thr Asp Ser Leu Val Val Ala Val Glu Glu Asp Val Lys Asn Asp
            580                 585                 590

Glu Val Ala Gln Val Glu Glu Leu Leu Glu Ser Glu Lys Val Glu Asn
            595                 600                 605

Gln Ser Ser Glu Leu Leu Ser Asp Thr Leu Ile Val Glu Ser Ala Asn
    610                 615                 620

Asp Lys Glu Glu Asp Arg Val Glu Ala Val Val Ser Glu Gln Pro Asp
625                 630                 635                 640

Ser Ile Pro His Gln Asn Val Glu Ile Ser Leu Val Glu Pro Thr Asn
                645                 650                 655

Val Glu Thr Glu Thr Val Val Thr Pro Ile Asn Asp Ala Ala Thr Pro
            660                 665                 670

His Gly Ser Pro Thr Tyr Ile Asp Asn Ser Val Thr Glu Ser Val Ala
            675                 680                 685

Thr Pro Leu Glu Lys Asp Ser Ile Gln Ala Gly Glu Thr Glu Ile Ala
    690                 695                 700

Glu Pro Thr Ser Ser Glu Ser Thr Asn Val Glu Thr Glu Thr Val Val
705                 710                 715                 720

Thr Pro Val Asn Asp Val Ala Thr Pro His Gly Ser Pro Thr Tyr Ile
                725                 730                 735

Asp Asn Ser Val Thr Glu Ser Val Ala Thr Pro Leu Glu Lys Asp Ser
            740                 745                 750

Ile Gln Ala Gly Glu Thr Glu Ile Ala Glu Pro Thr Ser Ser Glu Ser
            755                 760                 765

Thr Asn Val Glu Thr Glu Thr Val Val Thr Pro Val Asn Asp Val Ala
    770                 775                 780

Thr Pro His Gly Ser Pro Thr Tyr Ile Asp Asn Ser Val Thr Glu Ser
785                 790                 795                 800

Val Ala Thr Pro Leu Glu Lys Asp Ser Ile Gln Ala Gly Glu Thr Glu
                805                 810                 815

Ile Ala Glu Pro Thr Ser Ser Glu Ser Thr Ser Val Glu Ala Glu Leu
            820                 825                 830

Val Asp Asn Ser Glu Ile His Ala Ala Thr Ser Ser Val Thr Pro Cys
            835                 840                 845

Gly Ser Ser Ala Tyr Ala Asp Gly Ser Thr Thr Glu Ser Val Ala Thr
850                 855                 860

Pro Leu Glu Lys Asp Ser Ile Gln Thr Gly Asn Thr Glu Ile Ala Glu
865                 870                 875                 880

Pro Thr Ser Ser Lys Ser Thr Asn Val Glu Ala Ala Ser Val Asp Asn
                885                 890                 895

Ser Glu Ile His Ala Asp Ala Ser Leu Thr Ala Val Ser Ser Val Asn
            900                 905                 910

Leu Asp Asn Pro Val Ile Glu Pro Val Ala Ile Ser Leu Ile Gly Ser
            915                 920                 925

Lys Arg Asp Thr Asn Ala Glu Val Glu Val Ser Ser Leu Ser Lys Arg
    930                 935                 940

-continued

```
Glu Val Arg Lys Thr Asn Thr Asp Gly Leu Ile Ser Val Gln Ser Lys
945                 950                 955                 960

Val Ile Lys Lys Glu Leu Leu Glu Ser Ser Leu Ala Glu Ala Gly Ser
            965                 970                 975

Pro Leu Leu Glu Ala Thr Ile Ala Gln Ser Ser Asn Ser Asn Ser Thr
            980                 985                 990

Glu Ile Gly Met Ser Tyr Gln Asn Thr Val Leu Leu Glu Ser Asn Asn
        995                 1000                1005

Thr Glu Arg Gln Val Ser Lys Ala Glu Ile Val Met Glu His Lys
    1010                1015                1020

Glu Thr Glu Leu Val Glu Thr Val Ser Ser Ala Ser Glu Pro Val
    1025                1030                1035

Val Leu Val Glu Asn Ile Ser Gln Thr Ser Asn Asn Thr Ile Glu
    1040                1045                1050

Ser Gly Lys Asn Met Gly Val Gln Ser Gln Ala Gly Ala Lys Gln
    1055                1060                1065

Ile Leu Gly Val Glu Gln Ser Ser Lys Val Ser Thr Pro Thr Ser
    1070                1075                1080

Arg Gln Ile Met Gly Val Gly Leu Leu Thr Leu Val Leu Gly Ser
    1085                1090                1095

Ala Leu Gly Leu Leu Lys Lys Arg Arg Lys
    1100                1105
```

VACCINE FOR PROTECTION AGAINST STREPTOCOCCUS suis

CROSS-REFERENCE TO RELATED APPLICATIONS

This application is a National Stage application of International Patent Application No. PCT/EP2019/082196, filed Nov. 22, 2019, which claims priority to Patent Application No. EP18208081.2, filed Nov. 23, 2018.

REFERENCE TO SEQUENCE LISTING SUBMITTED ELECTRONICALLY

The sequence listing of the present application is submitted electronically via EFS-Web as an ASCII formatted sequence listing with a file name "24669USPCT-SEQTXT-04MAY2021.txt", with a creation date of May 4, 2021, and a size of 10 KB. This sequence listing submitted via EFS-Web is part of the specification and is herein incorporated by reference in its entirety.

GENERAL FIELD OF THE INVENTION

The invention pertains to the protection of young piglets against a pathogenic infection with Streptococcus suis.

BACKGROUND OF THE INVENTION

Streptococcus suis is a commensal and opportunistic pathogen of swine. In particular under stress, the bacterium may elicit a pathogenic infection and induce disease. Under modern pig producing conditions, major stress is induced for example by weaning of piglets and transport of young piglets. This has made Streptococcus suis to become a major swine pathogen. It is also an emerging zoonotic agent of human meningitis and streptococcal toxic shock-like syndrome. Streptococcus suis is a well-encapsulated pathogen and multiple serotypes have been described based on the capsular polysaccharide antigenic diversity. Streptococcus suis uses an arsenal of virulence factors to evade the host immune system. Together, these characteristics have challenged the development of efficacious vaccines to fight this important pathogen. Recently, an overview article has been published regarding vaccines against Streptococcus suis (Mariela Segura: "Streptococcus suis vaccines: candidate antigens and progress, in Expert Review of Vaccines, Volume 14, 2015, Issue 12, pages 1587-1608). In this review, clinical field information and experimental data have been compiled and compared to give an overview of the current status of vaccine development against Streptoccus suis as outlined here below.

Currently used vaccines are mainly whole-cell bacterins. However, field reports describe difficulty in disease control and management, and specially "vaccine failures" are common. Carrier pigs are the primary source of infection, and both vertical and horizontal transmission are involved in spread of the disease within a herd. Mixing of carrier animals with susceptible animals under stressful conditions such as weaning and transportation usually results in clinical disease. Early medicated weaning and segregated early weaning practices do not eliminate Streptococcus suis infection. Therefore, effective control measures to prevent disease will hinge on prophylactic/metaphylactic procedures (where allowed) and on vaccination. Currently, field immunization efforts have focused on the use of commercial or autogenous bacterins. These vaccine strategies have been applied to either piglets or sows. From weaning and onwards piglets are more susceptible to Streptococcus suis infections due to the stresses associated with weaning and also, the common subsequent transport. Therefore, prepartum immunization in sows is often used to try and convey passive immunity to piglets and provide protection against Streptococcus suis under these stressful circumstances early in life. Moreover, sow vaccination is less costly and labor intensive, thus representing an economical alternative to piglet vaccination. Yet, available results seem to indicate that sow vaccination with bacterins is also a matter of controversy. In many cases vaccinated sows, even when vaccinated twice before parturition, respond poorly or not at all to vaccination which results in low maternal immunity transferred to the litters. And even if maternal immunity is transferred at a sufficient level, in many cases the maternal antibodies are too low to provide protection in the most critical period of 4-7 weeks of age.

In piglets, autogenous bacterins are frequently used in the field, especially in Europe. They are prepared from the virulent strain isolated on the farm with clinical problems and applied to the same farm. One of the disadvantages of autogenous bacterins is that vaccine safety data are lacking and severe adverse reactions may occur. Sampling errors (due to using only one or two pigs or samples) may result in failure to identify a strain or serotype associated with a recent outbreak. This failure may be especially problematic in endemic herds. Finally, the most important dilemma of autogenous bacterins is that their actual efficacy has been poorly studied. As application of autogenous vaccines is empirical, it is not surprising that results obtained with these vaccines are inconsistent.

Other experimental vaccines are also described in the art. Kai-Jen Hsueh et al. show ("Immunization with Streptococcus suis bacterin plus recombinant Sao protein in sows conveys passive immunity to their piglets", in: BMC Veterinary Research, BMC series—open, inclusive and trusted, 13:15, 7 Jan. 2017) that a bacterin plus subunit might be a basis for successful vaccination of sows to confer protective immunity to their piglets.

Live attenuated vaccines have also been contemplated in the art. Non encapsulated isogenic mutants of Streptococcus suis serotype 2 have been clearly shown to be avirulent. Yet, a live vaccine formulation based on a non encapsulated serotype 2 mutant induced only partial protection against mortality and failed to prevent the development of clinical signs in pigs challenged with the wildtype strain (Wisselink H J, Stockhofe-Zurwieden N, Hilgers L A, et al. "Assessment of protective efficacy of live and killed vaccines based on a non-encapsulated mutant of Streptococcus suis serotype 2." in: Vet Microbiol. 2002, 84:155-168.)

In the last years, an extensive list of antigenic or immunogenic Streptococcus suis molecules has been reported, and most of these have been discovered through immuno proteomics using either convalescent sera from infected pigs or humans and/or laboratory-produced immune sera. WO2015/181356 (IDT Biologika GmbH) has shown that a full length IgM protease can elicit a very good protective immune response in piglets in a vaccination scheme of administering two doses of the IgM protease antigen either alone or in combination with a prime vaccination containing a bacterin. Next to this, a subunit comprising the highly conserved Mac-1 domain (representing only about 35% of the full length protein) is able to induce an immune response that is as effective (or even better) as the full length protein in a bactericidal assay, suggesting that this subunit will also induce a protective immune response in vivo. It is noted that WO2017/005913 (Intervacc AB) also describes the use of an IgM protease antigen (in particular, an IgM protease polypeptide fused to a nucleotidase) but only the property of being able to elicit a seroresponse has been shown. A protective effect for an IgM protease antigen is not shown in this international patent application.

OBJECT OF THE INVENTION

It is an object of the invention to provide an improved vaccine that is able to induce in a pig an immune response leading to improved protection against *Streptococcus suis* when compared to prior art vaccines, in particular the vaccines as known from WO2015/181356, i.e. the vaccine comprising a full length IgM protease or a subunit thereof comprising the MAC domain.

SUMMARY OF THE INVENTION

In order to meet the object of the invention a vaccine has been devised comprising an IgM protease antigen of *Streptococcus suis*, for use in a method for protecting a pig against *Streptococcus suis*, wherein the IgM protease antigen is a protein according to SEQ ID NO:1.

Surprisingly, it has been found that with this antigen, even better protection can be obtained than with the antigens as known from WO2015/181356. The new protein differs from the antigens as known from the '356 patent application as follows: with regard to the full length proteins as described in the '356 patent, the first part of the sequence of the known proteins is not present, representing either a sequence comprising a signal peptide (AA's 1-34 of SEQ ID NO:1 of the '356 patent), or a sequence comprising a His-tag (AA's 1-22 of SEQ ID NO:2 of the '356 patent). With regard to the MAC domain, the novel protein is far more complete representing about 97% of the full length protein instead of about 35%. The reason for the improved protection is not clear. It might be that presence of a peptide at the beginning of the sequence interferes with inducing an immune response, in particular since in a bacterium, it is highly likely that this part of the protein is exposed to the hydrophilic environment of the whole bacterium, since at the other end there is a hydrophobic tail. The improved protection with regard to the MAC domain might be related to a better immunogenic property of the current protein given its length.

The invention also pertains to the use of an IgM protease antigen of *Streptococcus suis* for the manufacture of a vaccine for protecting pigs against *Streptococcus suis*, and a method of providing protection.

It is noted that in a vaccine the antigen is typically combined with a pharmaceutically acceptable carrier, i.e. a biocompatible medium, viz. a medium that after administration does not induce significant adverse reactions in the subject animal, capable of presenting the antigen to the immune system of the host animal after administration of the vaccine. Such a pharmaceutically acceptable carrier may for example be a liquid containing water and/or any other biocompatible solvent or a solid carrier such as commonly used to obtain freeze-dried vaccines (based on sugars and/or proteins), optionally comprising immunostimulating agents (adjuvants). Optionally other substances such as stabilisers, viscosity modifiers or other components are added depending on the intended use or required properties of the vaccine.

DEFINITIONS

A vaccine is a pharmaceutical composition that is safe to administer to a subject animal, and is able to induce protective immunity in that animal against a pathogenic micro-organism, i.e. to induce a successful protection against the micro-organism.

An IgM protease antigen of *Streptococcus suis* is an enzyme that specifically degrades porcine IgM (and not porcine IgG or porcine IgA; Seele at al, in *Journal of Bacteriology*, 2013, 195 930-940; and in *Vaccine* 33:2207-2212; 5 May 2015), a protein denoted as IdeSsuis, or an immunogenic part thereof (typically having a length of at least about 30-35% of the full length enzyme).

Protection against a micro-organism is aiding in preventing, ameliorating or curing a pathogenic infection with that micro-organism or a disorder arising from that infection, for example to prevent or reduce one or more clinical signs resulting from the infection with the pathogen.

EMBODIMENTS OF THE INVENTION

In an embodiment, the vaccine is for protecting the pig against *Streptococcus suis* viremia. It was found that the present vaccine may provide significantly improved protection against viremia, i.e. infection of the blood with *Streptococcus suis*.

Next, although in the '356 patent a dose of at least 250 µg of antigen is used, it has been found that a dosis below 120 µg may suffice for arriving at protection against *Streptococcus suis*. The minimum amount is the amount at which protective immunity can still be obtained. This can be established by routine experimentation and depends i.a. on the required level of protection. For the current vaccine, a minimum amount is believed to be 1 µg of the antigen per dosis, but it may be any higher dosis such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or any higher integer in the range 61-119 up to 120 µg per dosis.

In an embodiment of the present invention the method consists of administering between 10 and 100 µg of the protein per dose, for example around 50 µg per dose. In another embodiment 3 of the vaccine for use according to the invention, the vaccine is administered twice.

The invention will now be further explained based on the following non-limiting examples.

EXAMPLE

Objective

The objective of this experiment was to test the efficacy of different IgM protease constructs in pigs against challenge with *Streptococcus suis* serotype 2. One construct consisted of a protein with his-tag (corresponding to SEQ ID NO:2 in the '356 patent), denoted as "356 full length". Another construct consisted of protein denoted as SEQ ID NO:1 in the '356 patent, but differing in that this protein does not have the first 34 amino acids (or his-tag), denoted as "fragment". This is the protein according to SEQ ID NO:1 of the current specification. A third construct consisted of the conserved unaltered MAC1 domain with his-tag, corresponding to the subunit denoted as SEQ ID NO:5 in the '356 patent, denoted "MAC1". To assess whether sequence variance would have any effect, the last construct consisted of the conserved with MAC1 domain with 15% artificially altered amino acids, having a his-tag, denoted as "MAC1 85%".

Study Design

Fifty 5-week-old seronegative SPF piglets were used. The piglets were allotted to five groups (evenly distributed over the different litters) of 10 piglets each. Groups 1 to 4 were vaccinated twice intramuscularly at 5 and 7 weeks of age with each of the different vaccines: 356 full length (group 1), fragment (group 2), MAC1 (group 3) and MAC1 85% (group 4). Each pig received a dose aiming at 50 µg per 2 ml of injected volume. Group 5 was left as unvaccinated challenge control. At 9 weeks of age the pigs were challenged intra-tracheally with a virulent culture of *S. suis* serotype 2. After challenge the pigs were observed daily for clinical signs of *S. suis* infection such as depression, locomotory problems and/or neurological signs during 11 days using a regular scoring system going from 0 (no signs) to 3 for severe cases. Animals reaching the humane endpoint after having shown specific clinical signs (i.e. locomotory or neurological) signs were euthanized without necropsy. Animals reaching the humane endpoint without having shown specific clinical signs were euthanized and necropsied including bacteriological examination to confirm the *S. suis* infection. Just before vaccination and challenge, serum blood was collected for antibody determination. At regular times before and after challenge heparin blood was collected from live animals for re-isolation of the challenge strain. If an animal was found dead before blood could be collected, the blood was not examined for the presence of *S. suis*.

Results

Only healthy pigs were used in the study. None of the vaccines induced any unacceptable site or systemic reactions and thus could be considered safe. The post challenge data for the period before scheduled day of necropsy (at day 11) are indicated in Table 1.

The data concern the average antibody titre measured at 7 and 9 weeks ("AT7" and "AT9") of age (4.3 is detection level, a level below was set at 3.3), the number of animals of which the blood was found to be infected with *Streptococcus suis* ("#PB"), the average clinical score during the test period ("CS"), the average survival time for all animals in a group ("ST"), the average time till death for the dead (when confirmed Ssuis positive) or euthanized animals ("TD"), and lastly the number of animals euthanized having specific clinical signs ("#E"). In group 2 (the "fragment" group), one animal was found dead one day after challenge before blood could be taken. This animal was found to be positive for *Streptococcus suis* after necropsy and bacteriological examination.

The results indicate that the novel protein, lacking the first part of the sequences as known from WO2015/181356, provides protection in pigs at least equally well, or even better, than the known IgM protease antigens. The antibody titer is consistently improved with respect to the known IgM protease antigens, and the same is true for all other parameters indicated in table 1. The effect is in particular significant for the comparison with the MAC domain proteins, although based on the bactericidal assays as described in WO2015/181356, it was not expected to find such a large difference in protective effect in vivo. The difference with the known full length protein observed for this small group of 10 animals, under practical circumstances, i.e. vaccination of large groups of pigs in large animal facilities, may result in a very significant improved level of protection. In particular the fact that no viremia (infection of the blood) could be detected in any of the animals vaccinated with the protein of the invention is a clear sign that this protein provides improved protection over the prior art proteins.

TABLE 1

Post challenge data

| Group | AT7 | AT9 | # PB | CS | ST | TD | # E |
|---|---|---|---|---|---|---|---|
| 356 full length | 5.9 | 10.2 | 3/10 | 23 | 8.4 | 2.3 | 3/10 |
| fragment | 6.9 | 10.6 | 0/9* | 21 | 8.7 | 3.3 | 2/10 |
| MAC1 | 3.9 | 5.5 | 6/10 | 57 | 4.3 | 1.7 | 7/10 |
| MAC1 85% | 3.5 | 5.3 | 5/10 | 44 | 6.0 | 1.4 | 6/10 |
| Control | 3.3 | 3.3 | 7/10 | 55 | 4.6 | 1.9 | 7/10 |

*One animal was found dead before blood could be collected

The invention claimed is:

1. A vaccine comprising a protein consisting of the amino acid sequence of SEQ ID NO:1 and a pharmaceutically acceptable carrier.

2. The vaccine of claim 1, wherein the vaccine comprises between 1 and 100 µg of the protein per dose.

3. The vaccine of claim 2, wherein the vaccine comprises between 1 and 50 µg of the protein per dose.

4. A method for protecting a pig against *Streptococcus suis*, by administering a vaccine comprising an IgM protease antigen of *Streptococcus suis* to the pig, wherein the protease antigen is a protein consisting of the amino acid sequence of SEQ ID NO:1.

5. The method of claim 4, wherein the vaccine is administered twice.

6. The method of claim 4, wherein the vaccine comprises less than 120 µg of the protein per dose.

7. The method of claim 6, wherein the vaccine is administered twice.

8. The method of claim 4, wherein the vaccine comprises a dose of between 10 and 100 µg of the protein.

9. The method of claim 8, wherein the vaccine is administered twice.

10. The method of claim 4, wherein the protecting of the pig against *Streptococcus suis* protects the pig against *Streptococcus suis* infection.

11. The method of claim 10, wherein the vaccine is administered twice.

12. The method of claim 10, wherein the vaccine comprises less than 120 µg of the protein per dose.

13. The method of claim 12, wherein the vaccine is administered twice.

14. The method of claim 10, wherein the vaccine comprises a dose of between 10 and 100 µg of the protein.

15. The method of claim 14, wherein the vaccine is administered twice.

* * * * *